(12) United States Patent
Basford et al.

(10) Patent No.: US 6,683,085 B2
(45) Date of Patent: Jan. 27, 2004

(54) SALT FORM AND POLYMORPHS

(75) Inventors: Patricia Ann Basford, Sandwich (GB); Paul Blaise Hodgson, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/797,112

(22) Filed: Mar. 1, 2001

(65) Prior Publication Data

US 2002/0010188 A1 Jan. 24, 2002

Related U.S. Application Data

(60) Provisional application No. 60/192,912, filed on Mar. 29, 2000, and provisional application No. 60/218,188, filed on Jul. 14, 2000.

(30) Foreign Application Priority Data

| Mar. 3, 2000 | (GB) | ............................................. 0005200 |
| Jun. 28, 2000 | (GB) | ............................................. 0015900 |

(51) Int. Cl.[7] .................... A61K 31/517; C07D 401/14
(52) U.S. Cl. ................... 514/266.21; 544/284
(58) Field of Search ............................ 514/260, 266.21; 544/284

(56) References Cited

U.S. PATENT DOCUMENTS 4,914,114 A    4/1990   Hausberg et al. ........... 546/273

FOREIGN PATENT DOCUMENTS

| WO | WO8801998 | 3/1988 |
| WO | WO9830560 | 7/1998 |

OTHER PUBLICATIONS

Lawrence X. Yu, et al., Pharmaceutical Research, vol. 20, No. 4, Apr. 2003pp. 531–536.*

* cited by examiner

*Primary Examiner*—John M. Ford
(74) *Attorney, Agent, or Firm*—Peter C. Richardson; Gregg C. Benson; Carl J. Goddard

(57) ABSTRACT

The present invention provides 4-amino-6,7-dimethoxy-2-(5-methanesulfonamido-1,2,3,4-tetrahydroisoquinol-2-yl)-5-(2-pyridyl)quinazoline mesylate of the formula

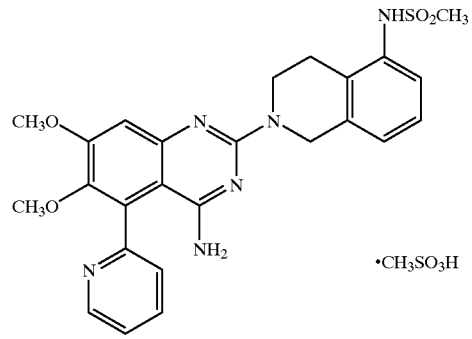

together with processes for preparing, and compositions containing it.

Figure 1:
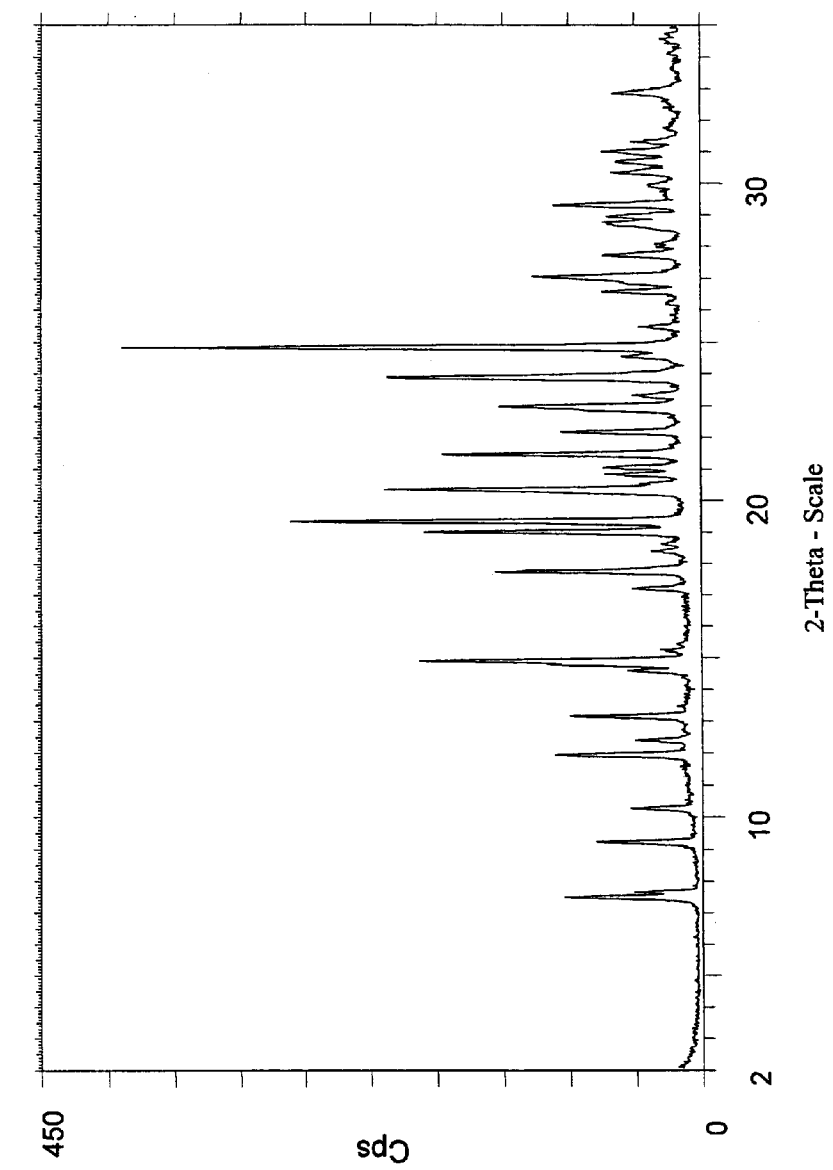

The invention also relates to substantially pure anhydrous crystalline polymorphic forms of the free base.

The compounds are particularly useful in the treatment of benign prostatic hyperplasia.

8 Claims, 11 Drawing Sheets

PXRD Pattern for the Mesylate Salt

DSC Thermogram for The Mesylate Salt

PXRD Patterns for All The Free Base Forms

DSC Thermogram for The Free Base Form A

DSC Thermogram for The Free Base Form B

DSC Thermogram for The Free Base Form C

DSC Thermogram for The Free Base Form E

DSC Thermogram for The Free Base Dihydrate, Form D

Moisture Sorption of The Mesylate Salt at 30°C

Moisture Sorption Isotherm for The Forms A, B and E

Moisture Sorption of The Free Base Form D (Di-Hydrate) at 30°C

SALT FORM AND POLYMORPHS

CROSS-REFERENCE TO RELATED APPLICATIONS

This application claims priority from U.S. provisional application No. 60/192,912, filed Mar. 29, 2000 and 60/218,188, filed Jul. 14, 2000.

NEW SALT FORM AND POLYMORPHS

The present invention relates to a novel salt useful in therapy. More specifically the present invention relates to 4-amino-6,7-dimethoxy-2-(5-methanesulfonamido-1,2,3,4-tetrahydroisoquinol-2-yl)-5-(2-pyridyl)quinazoline mesylate, to processes for its preparation, to its uses, and to compositions containing it. The present invention also relates to novel non-hydrated polymorphs of the free base.

4-Amino-6,7-dimethoxy-2-(5-methanesulfonamido-1,2,3,4-tetrahydroisoquinol-2-yl)-5-(2-pyridyl)quinazoline has the formula

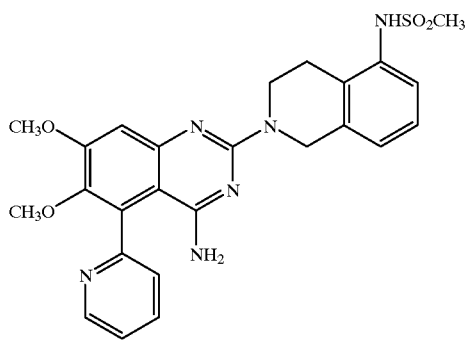

and is disclosed in WO 98/30560 (see Example 19) as being useful in the treatment of benign prostatic hyperplasia. The application refers in general terms to pharmaceutically acceptable salts and mentions the hydrochloride, hydrobromide and phosphate salts.

Unfortunately, 4-amino-6,7-dimethoxy-2-(5-methanesulfonamido-1,2,3,4-tetrahydroisoquinol-2-yl)-5-(2-pyridyl)quinazoline displays some disadvantageous physical properties. It is now known to occur in a number of different forms. In some cases, its aqueous solubility is rather low and it is difficult to prepare reproducibly in the same form, sometimes being obtained in a hydrated form. In addition, it has been found that some forms of the free base are rather hygroscopic. These properties are disadvantageous for the development of a drug substance because, in particular, a consistent grade of material must be reproducibly manufactured in order to satisfy regulatory requirements.

There is now provided the mesylate salt of 4-amino-6,7-dimethoxy-2-(5-methanesulfonamido-1,2,3,4-tetrahydroisoquinol-2-yl)-5-(2-pyridyl)quinazoline having the formula

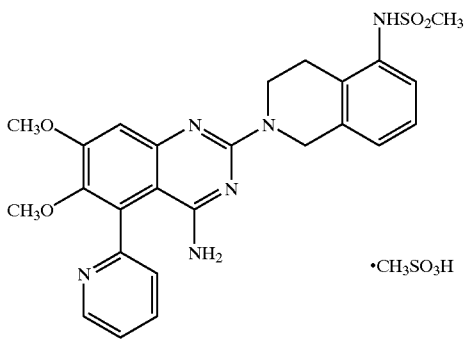

This substance has a number of unexpected advantages over the free base and it has surprisingly been found to have a unique combination of properties which make it ideal for development as a drug substance.

Those skilled in the art will appreciate that "mesylate" is an alternative term for "methanesulfonate".

The mesylate salt has a high melting point, and is a crystalline solid which does not display any hydrated or solvated forms. It is isomorphic, i.e. it exists in a single polymorphic form, and exhibits good stability over a wide range of conditions, e.g. high light intensity. It has acceptable solubility and dissolution characteristics, and can be economically prepared and processed to provide suitable solid dosage forms of the drug. Its hygroscopicity is substantially lower than the free base (tested as its 198° C. melting point polymorph) over a wide range of relative humidity. The mesylate salt is mono-morphic and does not form hydrates; both of these features represent advantageous properties of the mesylate salt in particular.

Tables 1 to 3 below indicate the physical properties of 4-amino-6,7-dimethoxy-2-(5-methanesulfonamido-1,2,3,4-tetrahydroisoquinol-2-yl)-5-(2-pyridyl)quinazoline mesylate and some free base forms.

TABLE 1

Physical properties of the mesylate salt

| Form | Melting Point (° C.) | Crystallinity | Hygroscopicity % (w/w) at 90% RH |
|---|---|---|---|
| Mesylate Salt | 279 | Crystalline | 1.1 |

TABLE 2

Solubility of the mesylate salt and free base forms (micrograms/ml)

| Solvent | Free base (mpt 198° C.) | Hydrated form of free base | Mesylate salt |
|---|---|---|---|
| Water at 22° C. | 420 | 12 | 880 |
| 0.9% sodium chloride at 22° C. | 36 | 4 | 120 |

TABLE 3

Hygroscopity of the mesylate salt and free base forms

| Form | Moisture sorption (% w/w) at 30° C. and 45% RH |
| --- | --- |
| Free base (mpt 198° C.) | 1.39 |
| Hydrated form of free base | 11.24 |
| Mesylate salt (mpt 279° C.) | 0.56 |

The present invention also includes the substantially pure anhydrous crystalline forms of 4-amino-6,7-dimethoxy-2-(5-methanesulfonamido-1,2,3,4-tetrahydroisoquinol-2-yl)-5-(2-pyridyl)quinazoline (the free base). These anhydrous polymorphs are designated Form A, Form B, Form C, and Form E in Table 4 below. Form D, which is presented for comparison, is the hydrated form and exists as a dihydrate.

The term "substantially pure" used above means that a sample of the relevant anhydrous crystalline form contains more than 90% of a single polymorphic form, preferably more than 99% of a single polymorphic form.

TABLE 4

Polymorphic forms of the free base

| Form | Melting point (° C.) | Crystallinity | Hygroscopity % (w/w) at 90% RH |
| --- | --- | --- | --- |
| Form A | 198 | crystalline | 2.2 |
| Form B | 218 | crystalline | 0.27 |
| Form C | 147 | crystalline | — |
| Form E | 229 | crystalline | 0.045 |
| Form D | None | crystalline | 12.8 |

On dehydration, the hydrated form (Form D) becomes amorphous.

The anhydrous polymorphic forms of the invention are also significantly less hygroscopic than the hydrated free base form. Of these, Forms B and E are preferred on account of their high melting points and low hygroscopicity. Form E is most preferred.

It is now believed that the solid form of 4-amino-6,7-dimethoxy-2-(5-methanesulfonamido-1,2,3,4-tetrahydroisoquinol-2-yl)-5-(2-pyridyl)quinazoline produced originally following the procedure of WO 98/30560 (see Example 19) was a mixture of Forms B and E, probably in the ratio 1:1 (based on a differential scanning calorimetry experiment showing sharp endotherms at 220 and 227° C.). Following the creation of the most stable Form E in pure form, it is likely that this form will be produced predominantly in the future when repeating the above preparation of 4-amino-6,7-dimethoxy-2-(5-methanesulfonamido-1,2,3,4-tetrahydroisoquinol-2-yl)-5-(2-pyridyl)quinazoline.

Also included within the scope of the present invention are radiolabelled derivatives, other isotopic forms and tautomers of 4-amino-6,7-dimethoxy-2-(5-methanesulfonamido-1,2,3,4-tetrahydroisoquinol-2-yl)-5-(2-pyridyl)quinazoline in the form of the anhydrous free base or the mesylate salt.

4-Amino-6,7-dimethoxy-2-(5-methanesulfonamido-1,2,3,4-tetrahydroisoquinol-2-yl)-5-(2-pyridyl)quinazoline in one of its free base polymorphic forms or as the mesylate salt possesses pharmacological activity in animals. It may be used in the treatment of a number of conditions including hypertension, myocardial infarction, male erectile dysfunction, hyperlipidaemia, cardiac arrhythmia and benign prostatic hyperplasia. The latter condition is of greatest interest. Thus, according to another aspect of the invention, there is provided a method of treatment of benign prostatic hyperplasia which comprises administering a therapeutically effective amount of 4-amino-6,7-dimethoxy-2-(5-methanesulfonamido-1,2,3,4-tetrahydroisoquinol-2-yl)-5-(2-pyridyl)quinazoline in the form of the anhydrous free base or the mesylate salt to a patient suffering from such a disorder.

According to a further aspect of the invention, there is provided 4-amino-6,7-dimethoxy-2-(5-methanesulfonamido-1,2,3,4-tetrahydroisoquinol-2-yl)-5-(2-pyridyl)-quinazoline in the form of the anhydrous free base or the mesylate salt for use as a pharmaceutical; and for use in the treatment of benign prostatic hyperplasia.

According to a further aspect of the invention, there is provided the use of 4-amino-6,7-dimethoxy-2-(5-methanesulfonamido-1,2,3,4-tetrahydroisoquinol-2-yl)-5-(2-pyridyl)-quinazoline in the form of the anhydrous free base or the mesylate salt in the manufacture of a medicament for the treatment of benign prostatic hyperplasia.

4-Amino-6,7-dimethoxy-2-(5-methanesulfonamido-1,2,3,4-tetrahydroisoquinol-2-yl)-5-(2-pyridyl)quinazoline in the form of the anhydrous free base or the mesylate salt can be administered alone but will generally be administered in admixture with a suitable pharmaceutical excipient, diluent or carrier selected with regard to the intended route of administration and standard pharmaceutical practice.

Hence, according to a further aspect of the invention, there is provided a pharmaceutical formulation including 4-amino-6,7-dimethoxy-2-(5-methanesulfonamido-1,2,3,4-tetrahydroisoquinol-2-yl)-5-(2-pyridyl)quinazoline in the form of the anhydrous free base or the mesylate salt in admixture with a pharmaceutically acceptable adjuvant, diluent or carrier. The formulation will preferably contain less than 50% by weight of 4-amino-6,7-dimethoxy-2-(5-methanesulfonamido-1,2,3,4-tetrahydroisoquinol-2-yl)-5-(2-pyridyl)quinazoline in a free base polymorphic form or as the mesylate salt.

For example, 4-amino-6,7-dimethoxy-2-(5-methanesulfonamido-1,2,3,4-tetrahydroisoquinol-2-yl)-5-(2-pyridyl)quinazoline in the form of the anhydrous free base or the mesylate salt can be administered orally, buccally or sublingually in the form of tablets, capsules, ovules, elixirs, solutions or suspensions, which may contain flavouring or colouring agents, for immediate-, delayed- or controlled-release applications. Oral administration is of particular interest. 4-Amino-6,7-dimethoxy-2-(5-methanesulfonamido-1,2,3,4-tetrahydroisoquinol-2-yl)-5-(2-pyridyl)quinazoline in the form of the anhydrous free base or the mesylate salt may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, 4-amino-6,7-dimethoxy-2-(5-methanesulfonamido-1,2,3,4-tetrahydroisoquinol-2-yl)-5-

(2-pyridyl)quinazoline in the form of the anhydrous free base or the mesylate salt may be combined with various sweetening or flavouring agents, colouring matter or dyes, with emulsifying and/or suspending agents and with diluents such as water, ethanol, propylene glycol and glycerin, and combinations thereof.

4-Amino-6,7-dimethoxy-2-(5-methanesulfonamido-1,2,3,4-tetrahydroisoquinol-2-yl)-5-(2-pyridyl)quinazoline in the form of the anhydrous free base or the mesylate salt can also be administered parenterally, for example, intravenously, intra-arterially, intraperitoneally, intrathecally, intraventricularly, intrasternally, intracranially, intramuscularly or subcutaneously, or may be administered by infusion techniques. It is best used in the form of a sterile aqueous solution which may contain other substances; for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of 4-amino-6,7-dimethoxy-2-(5-methanesulfonamido-1,2,3,4-tetrahydroisoquinol-2-yl)-5-(2-pyridyl)quinazoline in the form of the anhydrous free base or the mesylate salt will usually be from about 0.01 to 10 mg/kg (in single or divided doses) and preferably about 0.01 to 0.5 mg/kg, administered from 1 to 4 times a day.

Thus tablets or capsules of 4-amino-6,7-dimethoxy-2-(5-methanesulfonamido-1,2,3,4-tetrahydroisoquinol-2-yl)-5-(2-pyridyl)quinazoline in the form of the anhydrous free base or the mesylate salt may contain from about 0.1 mg to 500 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

4-Amino-6,7-dimethoxy-2-(5-methanesulfonamido-1,2,3,4-tetrahydroisoquinol-2-yl)-5-(2-pyridyl)quinazoline in the form of the anhydrous free base or the mesylate salt can also be administered intranasally or by inhalation and is conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HEFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of 4-amino-6,7-dimethoxy-2-(5-methanesulfonamido-1,2,3,4-tetrahydroisoquinol-2-yl)-5-(2-pyridyl)quinazoline in the form of the anhydrous free base or the mesylate salt and a suitable powder base such as lactose or starch.

Aerosol or dry powder formulations are preferably arranged so that each metered dose or "puff" contains from 20 µg to 4 mg of 4-amino-6,7-dimethoxy-2-(5-methanesulfonamido-1,2,3,4-tetrahydroisoquinol-2-yl)-5-(2-pyridyl)quinazoline in the form of the anhydrous free base or the mesylate salt for delivery to the patient. The overall daily dose with an aerosol will be in the range of from 20 µg to 20 mg which may be administered in a single dose or, more usually, in divided doses throughout the day.

Alternatively, 4-amino-6,7-dimethoxy-2-(5-methanesulfonamido-1,2,3,4-tetrahydroisoquinol-2-yl)-5-(2-pyridyl)quinazoline in the form of the anhydrous free base or the mesylate salt can be administered in the form of a suppository or pessary, or may be applied topically in the form of a lotion, solution, cream, ointment or dusting powder.

4-Amino-6,7-dimethoxy-2-(5-methanesulfonamido-1,2,3,4-tetrahydroisoquinol-2-yl)-5-(2-pyridyl)quinazoline in the form of the anhydrous free base or the mesylate salt may also be transdermally administered, for example, by the use of a skin patch. It may also be administered by the ocular route, particularly for treatment of the eye.

For ophthalmic use, it can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, it may be formulated in an ointment such as petrolatum.

For application topically to the skin, 4-amino-6,7-dimethoxy-2-(5-methanesulfonamido-1,2,3,4-tetrahydroisoquinol-2-yl)-5-(2-pyridyl)quinazoline in the form of the anhydrous free base or the mesylate salt can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The invention further provides a process for the preparation of 4-amino-6,7-dimethoxy-2-(5-methanesulfonamido-1,2,3,4-tetrahydroisoquinol-2-yl)-5-(2-pyridyl) quinazoline mesylate, as defined above, which comprises the addition of methanesulphonic acid to a suspension or solution of 4-amino-6,7-dimethoxy-2-(5-methanesulfonamido-1,2,3,4-tetrahydroisoquinol-2-yl)-5-(2-pyridyl)quinazoline of the formula

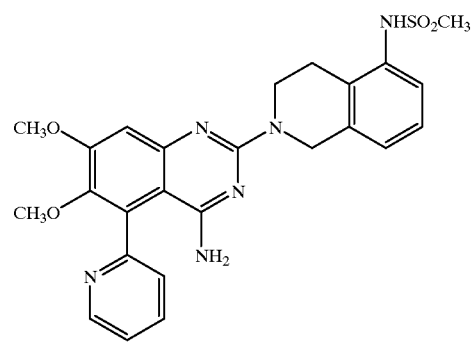

in a suitable solvent, and collection of the precipitated solid.

Preferred features of the process include:

(a) the solution of 4-amino-6,7-dimethoxy-2-(5-methanesulfonamido-1,2,3,4-tetrahydroisoquinol-2-yl)-5-(2-pyridyl)quinazoline is maintained at a temperature above room temperature before the addition of the methanesulphonic acid; and (b) the solvent used is a mixture of butanone and water, for example a 10:1 by volume mixture of butanone and water.

The process may be defined more particularly as a process comprising the steps of:

(a) heating a suspension of 4-amino-6,7-dimethoxy-2-(5-methanesulfonamido-1,2,3,4-tetrahydroisoquinol-2-yl)-5-(2-pyridyl)quinazoline in butanone/water to reflux;

(b) adding butanone/water until a solution is achieved;

(c) cooling the solution;

(d) adding methanesulfonic acid; and (e) collecting the resulting solid by filtration.

In the above processes, it is preferred that the 4-amino-6,7-dimethoxy-2-(5-methanesulfonamido-1,2,3,4-tetrahydroisoquinol-2-yl)-5-(2-pyridyl)quinazoline is present as Form E, although some of the desired product should result regardless of the starting form.

The formulations of the invention may also contain a human 5-α reductase inhibitory compound [see International Patent Application WO-A-95/28397], or 4-amino-6,7-dimethoxy-2-(5-methanesulfonamido-1,2,3,4-tetrahydroisoquinol-2-yl)-5-(2-pyridyl)quinazoline in the form of the anhydrous free base or the mesylate salt could be presented in a pharmaceutical pack also containing a human 5-α reductase inhibitory compound as a combined preparation for simultaneous, separate or sequential use.

References herein to treatment include curative, palliative and prophylactic treatment.

The four anhydrous polymorphs of the free base which have been isolated have been designated Forms A, B, C and E. These polymorphic forms were characterised by powder X-ray diffraction (PXRD), together with the mesylate salt.

The powder X-ray diffraction patterns were determined using a SIEMENS D5000 powder X-ray diffractometer fitted with an automatic sample changer, a theta—theta goniometer, automatic beam divergence slits, a secondary monochromator and a scintillation counter. The samples were prepared for analysis by packing the powder into 12 mm diameter, 0.25 mm deep cavities that had been cut into silicon wafer specimen mounts. Each specimen was rotated whilst being irradiated with copper K-alpha$_1$ X-rays (wavelength=1.5406 Angstroms) with the X-ray tube operated at 40 kV/40 mA. The analyses were performed with the goniometer running in step-scan mode set for a 5 second count per 0.02° step over a two theta range of 2° to 55°. The peak intensities are summarised in Table 5. In Table 5, "Angle 2-Theta" is related to the interplanar spacing of the crystal, and the intensity is given as a percentage of the greatest peak ($I/I_1$). The individual polymorphic forms and the mesylate salt may be characterised by reference to the peak intensities of greater than 50%, and more preferably by the peaks having intensities greater than 20%.

TABLE 5

Peak listings for Forms A, B, C and E, and the mesylate salt

| Angle 2-Theta ° | Intensity % | Angle 2-Theta ° | Intensity % | Angle 2-Theta ° | Intensity % | Angle 2-Theta ° | Intensity % |
|---|---|---|---|---|---|---|---|
| Form A | | | | | | | |
| 6.002 | 21.1 | 15.669 | 4.7 | 23.282 | 40.8 | 30.469 | 15.3 |
| 8.893 | 22.9 | 17.040 | 30.0 | 23.494 | 37.3 | 31.498 | 17.4 |
| 9.401 | 25.1 | 17.888 | 33.4 | 23.884 | 92.4 | 32.257 | 8.8 |
| 9.654 | 8.5 | 18.111 | 16.7 | 24.298 | 42.7 | 33.063 | 11.6 |
| 11.105 | 33.4 | 18.872 | 51.9 | 24.554 | 18.7 | 33.797 | 14.1 |
| 12.000 | 100.0 | 19.287 | 18.9 | 24.602 | 19.6 | 34.889 | 17.1 |
| 12.071 | 50.2 | 19.336 | 16.0 | 25.674 | 30.1 | 35.158 | 21.2 |
| 13.060 | 25.1 | 19.714 | 7.2 | 26.087 | 13.8 | 35.610 | 12.5 |
| 13.373 | 10.3 | 20.126 | 6.5 | 26.600 | 19.1 | 36.226 | 13.8 |
| 13.458 | 11.6 | 20.951 | 15.3 | 27.036 | 11.8 | 36.634 | 12.4 |
| 13.620 | 10.0 | 21.021 | 12.9 | 27.641 | 24.4 | 38.335 | 16.0 |
| 13.708 | 15.5 | 21.302 | 15.4 | 28.888 | 18.3 | 40.198 | 17.2 |
| 13.790 | 10.8 | 21.378 | 19.9 | 29.136 | 14.6 | 40.820 | 13.7 |
| 14.418 | 10.9 | 21.925 | 57.5 | 29.915 | 9.4 | 41.279 | 15.7 |
| 15.075 | 4.3 | 22.346 | 94.6 | 30.197 | 19.4 | 43.943 | 20.5 |
| 15.320 | 6.1 | 22.821 | 22.7 | 30.282 | 25.8 | | |
| Form B | | | | | | | |
| 6.943 | 1.4 | 19.559 | 8.4 | 26.512 | 36.5 | 34.214 | 9.3 |
| 9.004 | 37.5 | 19.867 | 11.1 | 26.758 | 30.5 | 34.382 | 12.2 |
| 9.725 | 41.2 | 19.964 | 6.1 | 26.918 | 20.7 | 34.602 | 7.7 |
| 10.526 | 40.7 | 20.407 | 62.2 | 26.989 | 25.4 | 35.235 | 10.4 |
| 11.315 | 3.4 | 20.919 | 31.2 | 27.302 | 7.2 | 35.449 | 13.0 |

TABLE 5-continued

Peak listings for Forms A, B, C and E, and the mesylate salt

| Angle 2-Theta ° | Intensity % | Angle 2-Theta ° | Intensity % | Angle 2-Theta ° | Intensity % | Angle 2-Theta ° | Intensity % |
|---|---|---|---|---|---|---|---|
| 11.986 | 2.1 | 21.101 | 17.3 | 27.800 | 17.4 | 36.193 | 6.8 |
| 13.011 | 2.2 | 21.712 | 14.4 | 27.871 | 11.6 | 36.668 | 8.1 |
| 13.493 | 30.2 | 22.551 | 72.7 | 28.945 | 9.5 | 37.331 | 12.6 |
| 13.897 | 74.4 | 22.769 | 20.2 | 29.164 | 14.4 | 37.727 | 8.4 |
| 14.306 | 3.3 | 22.843 | 13.9 | 30.027 | 7.5 | 38.318 | 5.4 |
| 15.569 | 25.2 | 22.926 | 15.3 | 30.284 | 10.2 | 38.977 | 11.3 |
| 15.883 | 48.3 | 23.418 | 100.0 | 31.179 | 19.9 | 39.646 | 15.8 |
| 16.740 | 5.9 | 23.904 | 24.9 | 31.443 | 10.2 | 40.165 | 7.8 |
| 17.122 | 30.0 | 23.997 | 24.5 | 31.629 | 8.7 | 40.911 | 5.3 |
| 17.407 | 12.3 | 25.049 | 21.4 | 32.121 | 8.1 | 42.235 | 10.8 |
| 17.603 | 5.7 | 25.209 | 32.4 | 32.318 | 7.9 | 42.761 | 9.8 |
| 18.094 | 4.1 | 25.462 | 17.0 | 32.845 | 12.2 | 44.287 | 7.2 |
| 18.727 | 62.9 | 25.700 | 8.4 | 33.023 | 14.8 | 44.775 | 9.5 |
| 19.176 | 10.0 | 26.205 | 12.9 | 34.045 | 9.5 | | |
| | | | | Form C | | | |
| 5.510 | 4.2 | 17.488 | 24.7 | 25.257 | 52.6 | 31.939 | 28.9 |
| 6.143 | 4.4 | 18.601 | 76.6 | 25.885 | 19.4 | 32.689 | 14.9 |
| 7.860 | 63.2 | 18.964 | 32.9 | 26.283 | 22.0 | 33.228 | 13.6 |
| 8.141 | 13.2 | 19.230 | 16.8 | 26.634 | 28.5 | 33.880 | 16.4 |
| 9.774 | 8.0 | 19.727 | 51.4 | 27.085 | 17.6 | 34.867 | 15.1 |
| 10.290 | 12.0 | 20.121 | 29.0 | 27.309 | 20.8 | 35.627 | 16.9 |
| 11.076 | 6.9 | 20.440 | 10.1 | 27.574 | 28.7 | 36.765 | 14.7 |
| 11.262 | 6.3 | 20.859 | 14.5 | 27.904 | 19.1 | 37.551 | 19.7 |
| 12.133 | 24.3 | 21.261 | 19.4 | 28.165 | 14.3 | 38.576 | 20.2 |
| 12.510 | 7.5 | 21.730 | 100.0 | 28.891 | 19.3 | 39.190 | 23.3 |
| 12.860 | 14.2 | 22.310 | 39.0 | 29.226 | 15.1 | 40.302 | 16.8 |
| 13.690 | 37.3 | 22.830 | 72.0 | 29.792 | 30.7 | 40.824 | 16.8 |
| 14.446 | 8.5 | 23.102 | 27.7 | 30.101 | 19.7 | 41.643 | 15.1 |
| 15.008 | 35.4 | 23.598 | 75.9 | 30.287 | 15.7 | 42.238 | 16.6 |
| 15.794 | 32.6 | 23.884 | 24.7 | 30.604 | 17.0 | 42.971 | 19.4 |
| 16.274 | 27.9 | 24.479 | 50.5 | 30.771 | 16.9 | 44.714 | 16.4 |
| 16.781 | 14.6 | 24.777 | 21.2 | 30.995 | 11.5 | | |
| 16.940 | 10.7 | 25.093 | 59.3 | 31.590 | 22.4 | | |
| | | | | Form E | | | |
| 8.416 | 6.3 | 18.028 | 12.3 | 23.852 | 100.0 | 32.434 | 14.8 |
| 8.506 | 3.9 | 18.387 | 6.4 | 24.075 | 18.0 | 32.760 | 25.6 |
| 9.675 | 23.0 | 18.787 | 17.0 | 24.192 | 18.9 | 34.083 | 8.6 |
| 11.994 | 15.7 | 19.315 | 38.5 | 24.696 | 10.7 | 34.462 | 7.8 |
| 12.393 | 13.7 | 19.358 | 42.2 | 25.280 | 28.2 | 34.927 | 5.6 |
| 13.116 | 8.2 | 19.444 | 31.1 | 25.765 | 11.1 | 35.552 | 7.1 |
| 13.952 | 16.4 | 19.778 | 26.6 | 26.061 | 12.1 | 36.390 | 7.2 |
| 14.064 | 17.2 | 20.056 | 6.9 | 26.746 | 8.5 | 36.954 | 6.3 |
| 15.978 | 5.8 | 20.398 | 3.5 | 27.269 | 10.6 | 37.993 | 7.1 |
| 16.096 | 3.7 | 21.522 | 7.5 | 28.860 | 13.0 | 39.826 | 4.7 |
| 16.218 | 3.6 | 21.770 | 7.7 | 29.534 | 5.3 | 40.699 | 8.4 |
| 16.914 | 30.8 | 22.479 | 8.2 | 29.642 | 7.9 | 42.316 | 7.0 |
| 17.042 | 13.4 | 22.974 | 5.0 | 31.094 | 4.3 | 43.410 | 7.0 |
| 17.596 | 10.3 | 23.509 | 7.0 | 31.652 | 4.0 | | |
| | | | | Mesylate salt | | | |
| 7.392 | 22.9 | 19.297 | 57.9 | 26.55 | 16.8 | 34.607 | 6.7 |
| 7.56 | 12.1 | 20.265 | 51 | 26.818 | 15.3 | 35.031 | 8.4 |
| 9.129 | 18.4 | 20.494 | 7.3 | 27.012 | 30.3 | 35.834 | 9.6 |
| 10.179 | 11 | 20.772 | 13.8 | 27.675 | 15.9 | 36.125 | 9.2 |
| 11.871 | 17.8 | 21.018 | 15.1 | 28.673 | 22.3 | 36.418 | 9.3 |
| 12.343 | 7.6 | 21.414 | 40 | 28.904 | 16.3 | 37.675 | 10 |
| 13.057 | 18.6 | 22.136 | 24 | 29.305 | 24.6 | 38.92 | 6.3 |
| 14.5 | 11.1 | 22.804 | 16.7 | 29.627 | 9.1 | 40.614 | 5.9 |
| 14.733 | 22.6 | 22.934 | 32.8 | 29.93 | 9.3 | 41.061 | 8.8 |
| 14.813 | 40.1 | 23.283 | 8.7 | 30.327 | 14.9 | 41.65 | 13.3 |
| 15.162 | 5.4 | 23.842 | 49.4 | 30.663 | 16.8 | 42.03 | 10.4 |
| 17.155 | 10.6 | 24.5 | 14.4 | 30.999 | 16.7 | 42.65 | 10.1 |
| 17.694 | 31 | 24.795 | 100 | 31.297 | 12.8 | 42.878 | 8.9 |
| 18.358 | 6.5 | 25.452 | 7.6 | 31.841 | 6 | 44.003 | 7.7 |
| 18.602 | 6.1 | 26.201 | 5.2 | 32.844 | 16.5 | 44.817 | 9.3 |
| 18.964 | 40.5 | | | | | | |

Differential scanning calorimetry (DSC) was performed using a Perkin Elmer DSC-7 machine fitted with an automatic sample changer. Approximately 2 mg of each sample was accurately weighed into a 50 microlitre aluminium pan and crimp sealed with a perforated lid. The samples were heated at 20° C./minute over the range 40° C. to 300° C.

with a nitrogen gas purge. The thermal events are summarised in Table 6, and may be used to characterize the free base forms and mesylate salt.

TABLE 6

Thermal Events for Forms A, B, C, E and the mesylate salt

| Form | Melting point (° C.) |
| --- | --- |
| Form A | 198 |
| Form B | 218 |
| Form C | 147 |
| Form E | 229 |
| Mesylate | 279 |

The water content of the hydrated form of the free base (Form D) at ambient conditions is commonly of the order of 9 to 10% (w/w). This is equivalent to 2.5 to 2.8 moles of water per mole of the free base. The water content at 90% RH was found to be 12.8% (w/w), this is equivalent to 3.6 moles of water, only 2 moles of which were found to represent bound water. The first mole was lost below 5% RH the second retained down to 1% RH see FIG. 11. It is likely that extended storage of the hydrated form below about 18% RH would result in dehydration. Furthermore, removal of the crystalline water results in the loss of the crystal lattice, the product being predominantly amorphous. This highlights a potential problem in using the conventional hydrated form in manufacturing a pharmaceutical formulation. Dehydration was observed on thermal analysis as a broad double endotherm at 97/113° C. (See FIG. 8)

Figure 2:
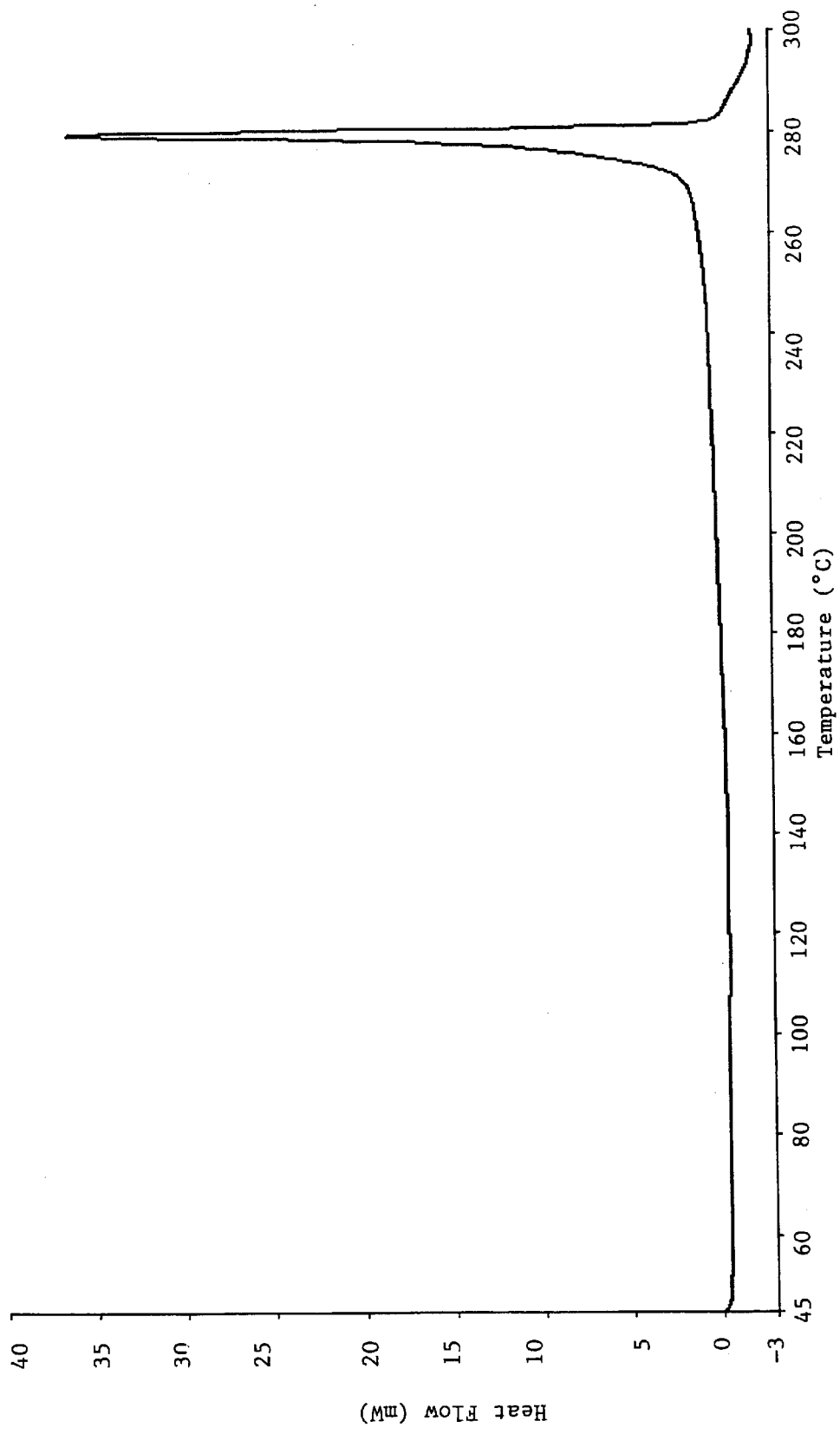
Figure 3:
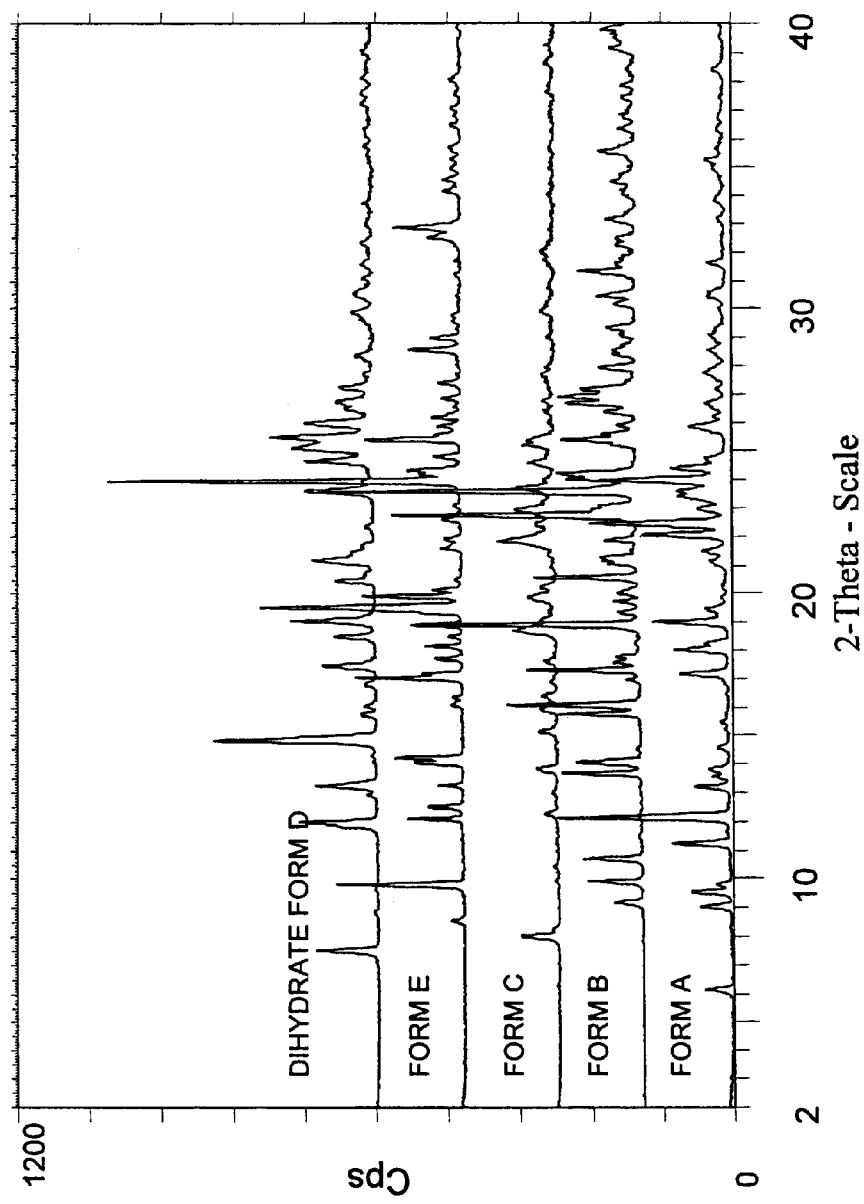
Figure 4:
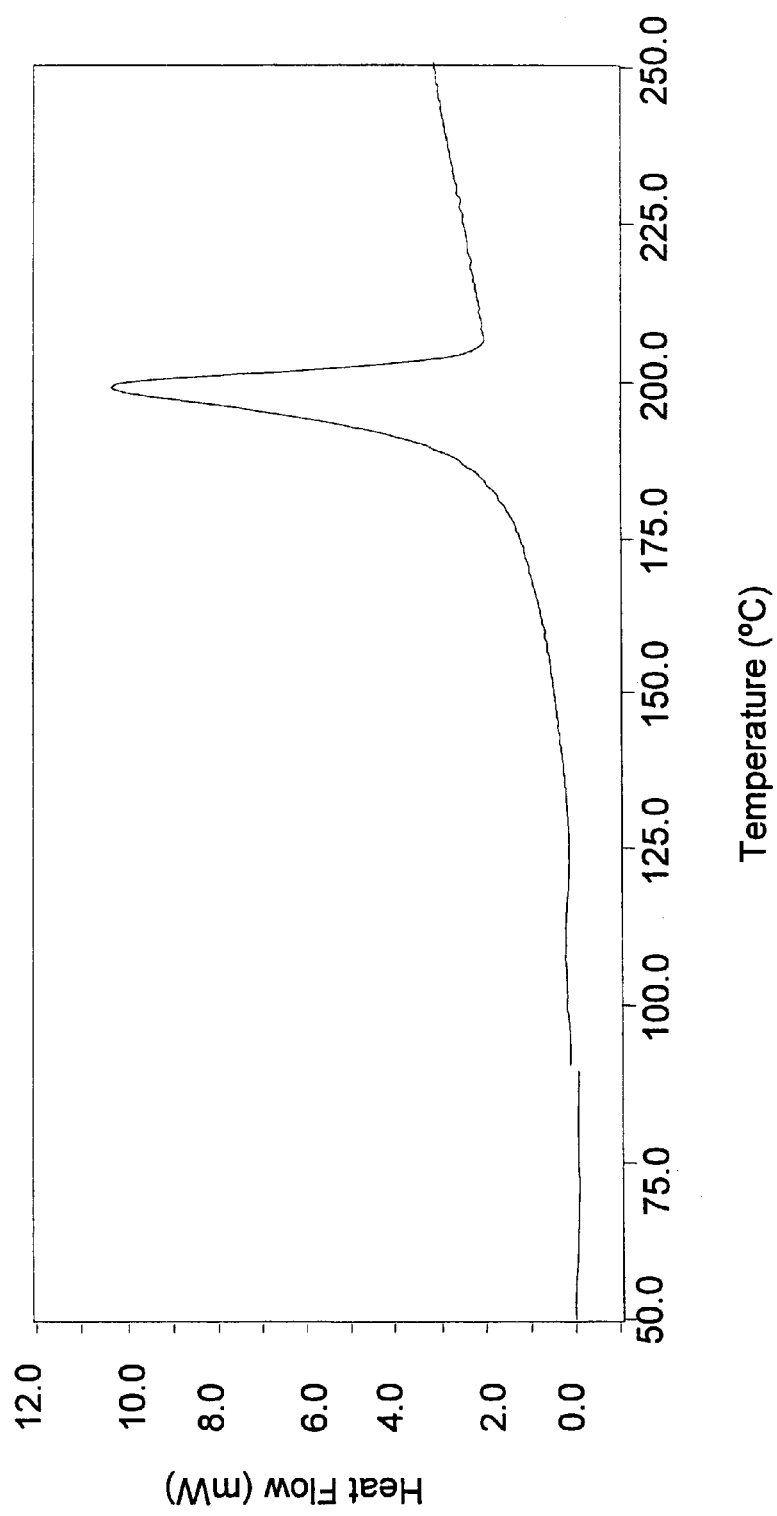
Figure 5:
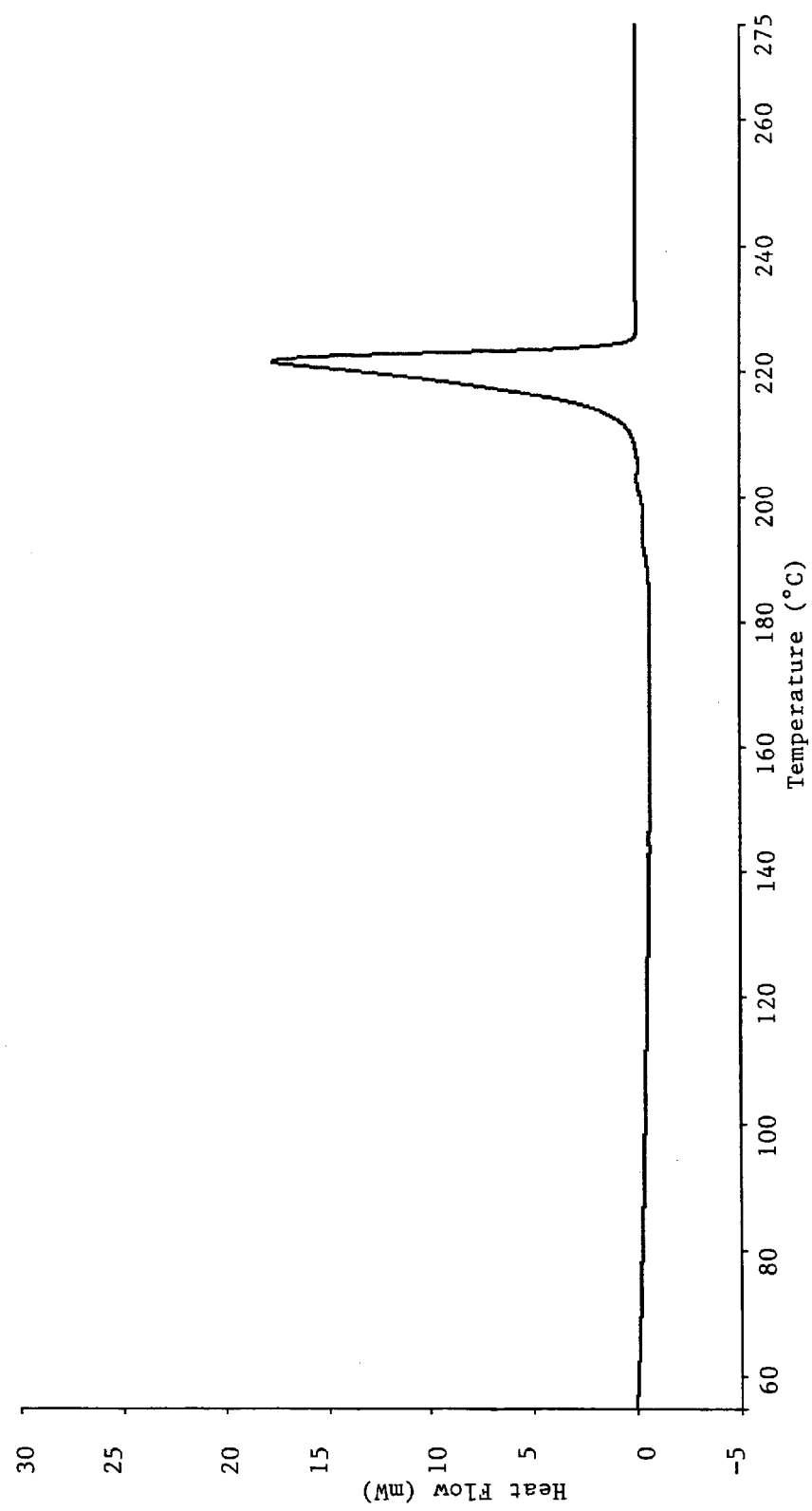
Figure 6:
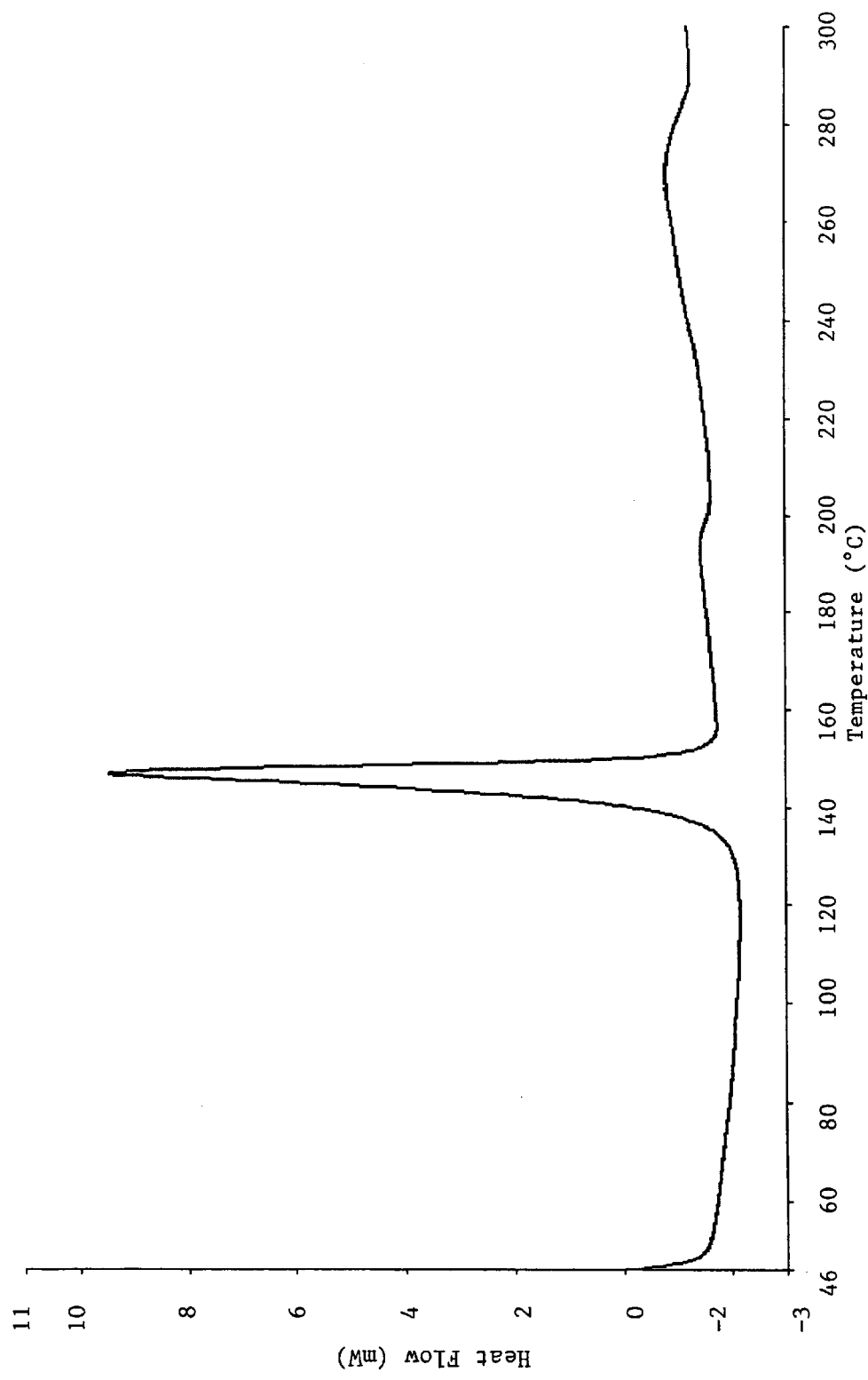
Figure 7:
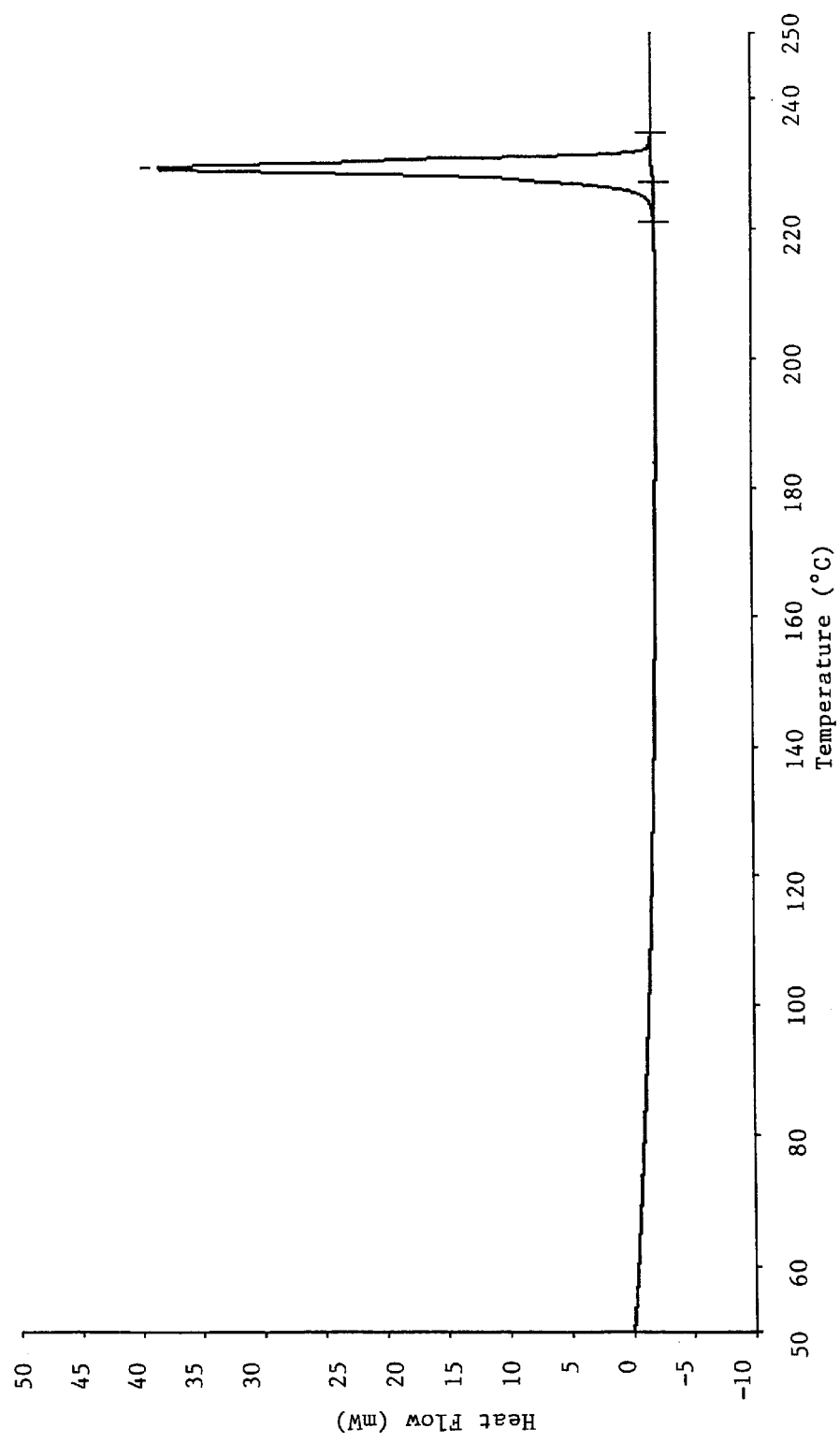
Figure 8:
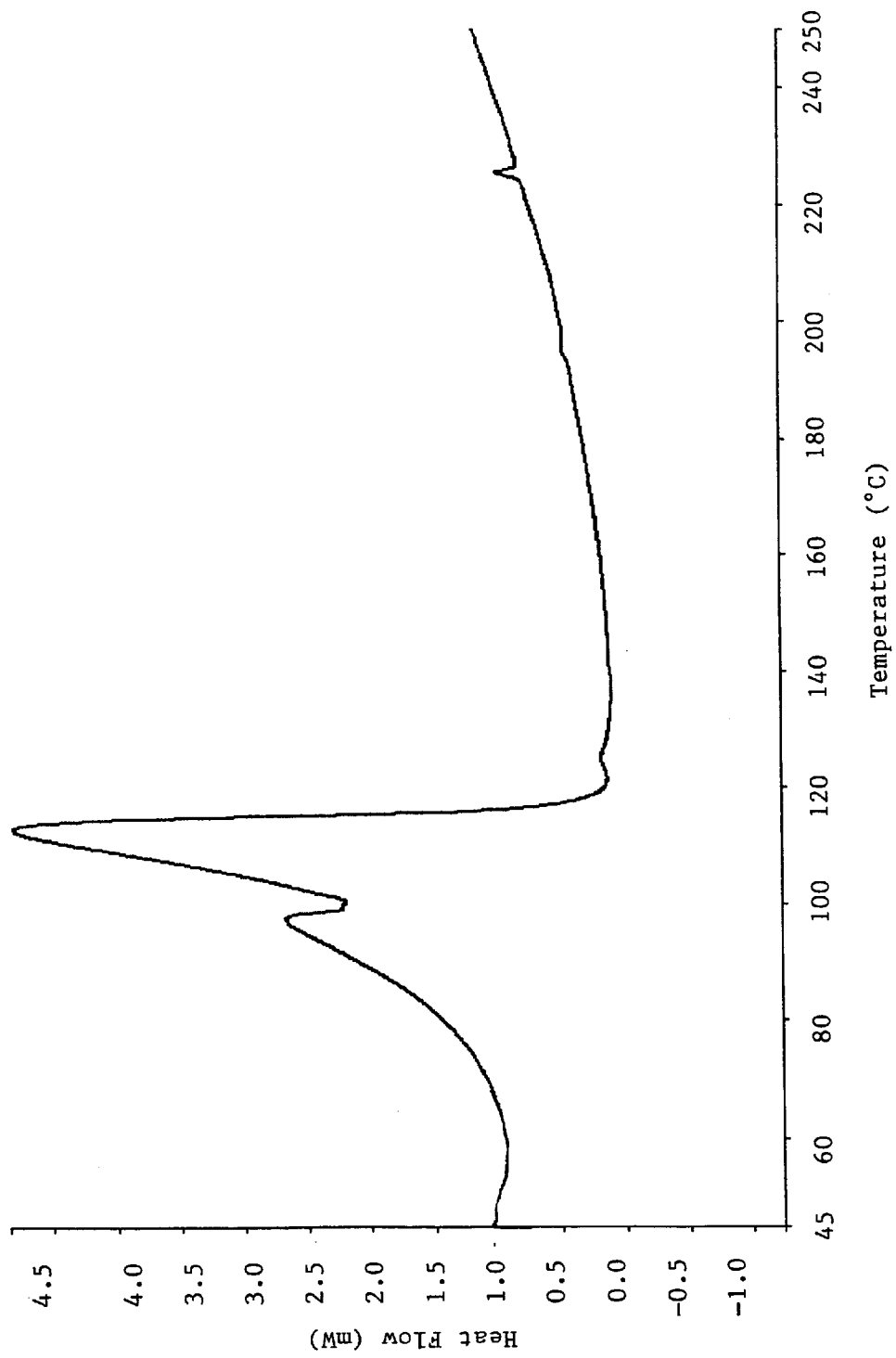
Figure 9:
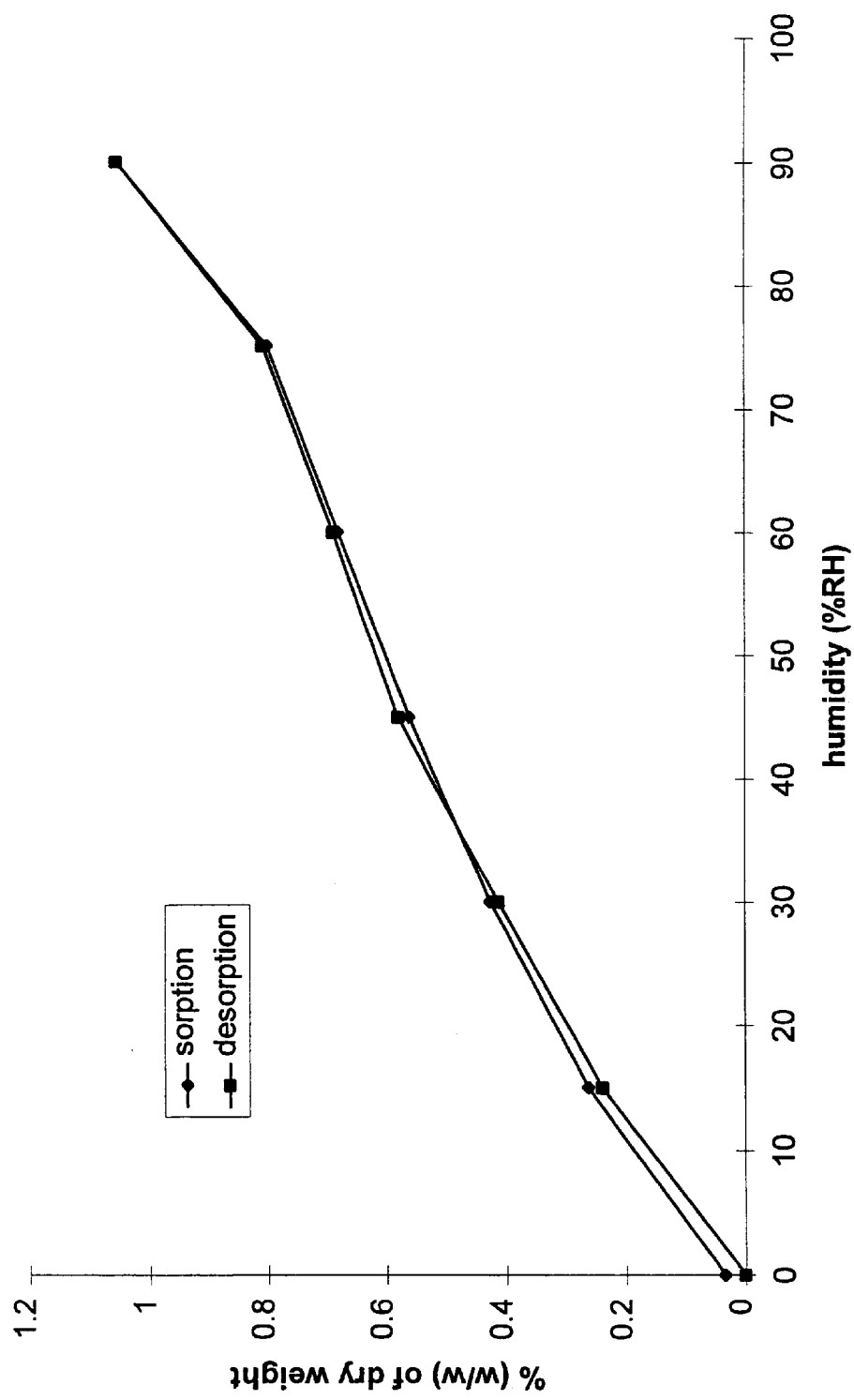
Figure 10:
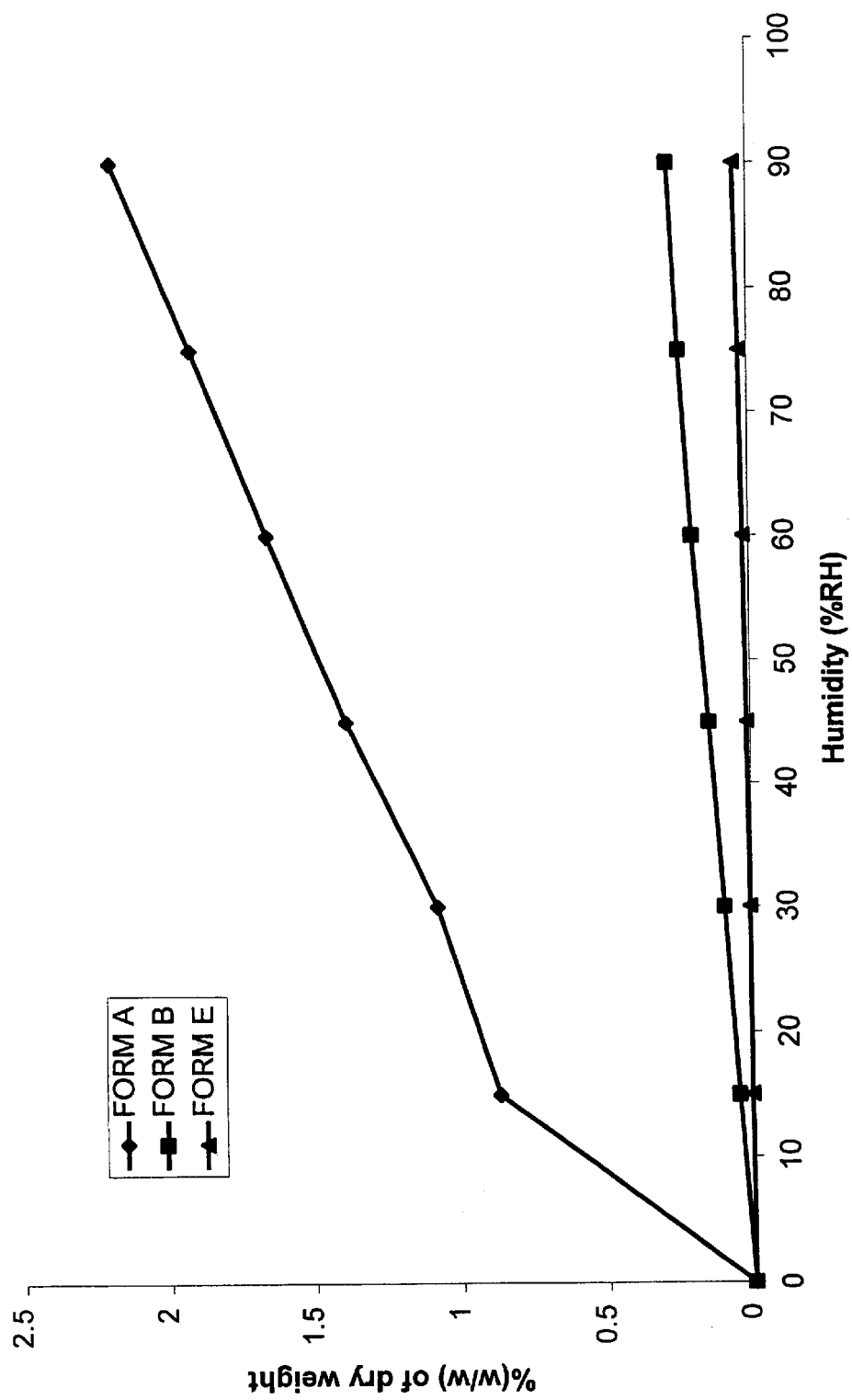
Figure 11:
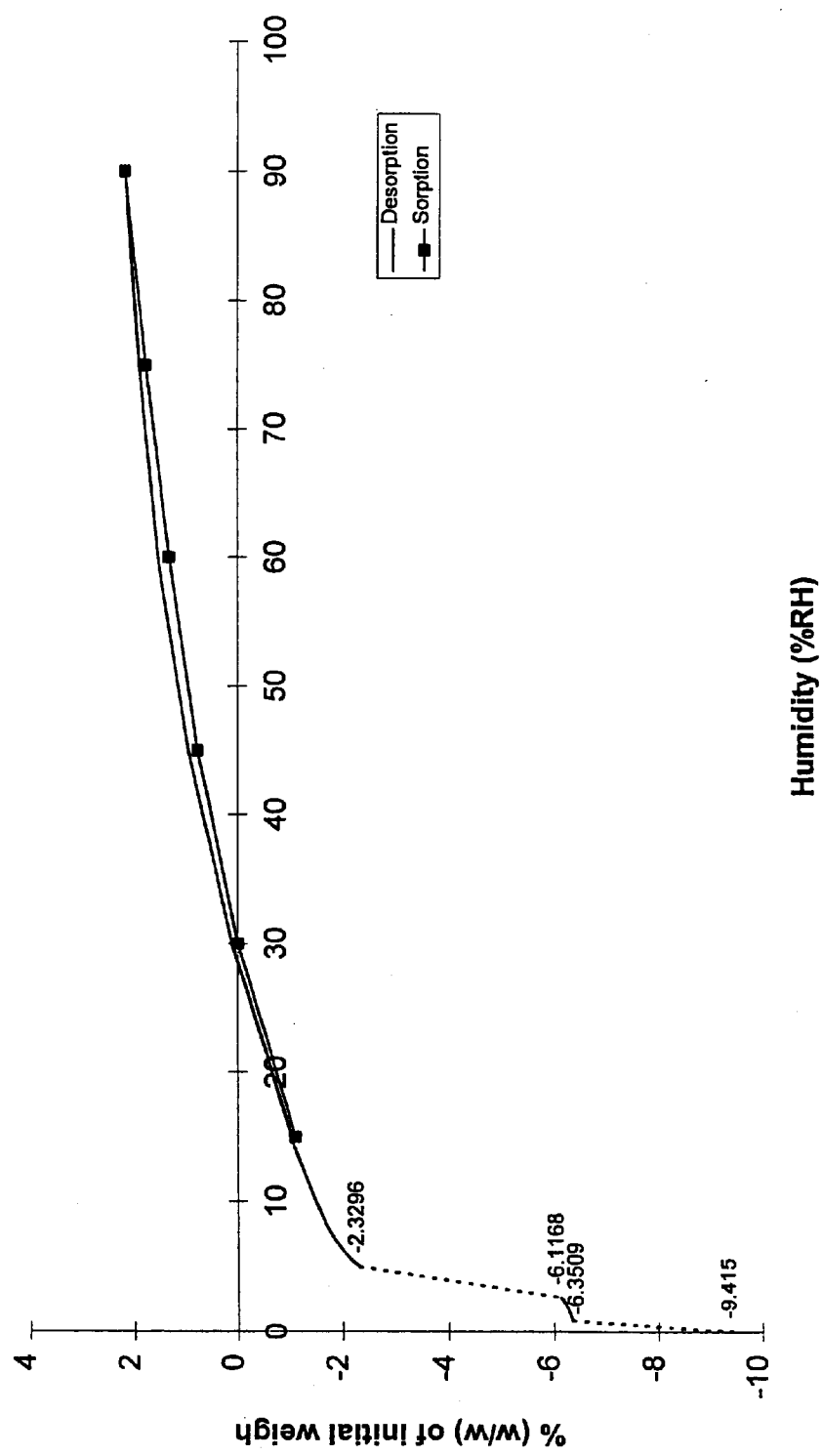

The present invention is also illustrated by the following drawings in which:

FIG. 1 shows the PXRD for the mesylate salt;
FIG. 2 shows the DSC thermogram for the mesylate salt;
FIG. 3 shows the PXRD for all the free base forms A, B, C, D and E;
FIG. 4 shows the DSC thermogram for Form A;
FIG. 5 shows the DSC thermogram for Form B;
FIG. 6 shows the DSC thermogram for Form C;
FIG. 7 shows the DSC thermogram for Form E;
FIG. 8 shows the DSC thermogram for form D;
FIG. 9 shows the moisture sorption of the mesylate salt;
FIG. 10 shows the moisture sorption of Forms A, B and E; and
FIG. 11 shows the moisture sorption of Form D.

The invention is illustrated by the Examples below, in which the following abbreviations may be used:

| | |
| --- | --- |
| min | minute |
| NMR | nuclear magnetic resonance |
| h | hour |

Example 1
Free Base Polymorphs of 4-Amino-6,7-dimethoxy-2-(5-methanesulfonamido-1,2,3,4-tetrahydro-2-isoquinolyl)-5-(2-pyridyl)quinazoline
(i) Form A Under nitrogen, to a stirred suspension of 4-amino-2-chloro-6,7-dimethoxy-5-(2-pyridyl)quinazoline [see WO 98/30560, Example 12(a), 97 g, 0.31 mol] and N-(1,2,3,4-tetrahydro-5-isoquinolyl)methanesulfonamide hydrochloride [see WO 98/30560, Example 19(b), 89 g, 0.34 mol] in n-butanol (1.91) was added triethylamine (161 ml, 1.16 mol). The reaction was warmed to reflux and stirred at reflux overnight. The reaction mixture was cooled to room temperature, concentrated in vacuo and the residue slurried in water (1.51) and sodium hydrogen carbonate (15 g) added. The resulting slurry was stirred over 3 nights, filtered, the solid washed with water (500 ml) and dried overnight in vacuo at 50° C. to give 158 g of material.

The majority of the material (156 g) was combined with a further portion of material (139 g) prepared using a similar method and the combined solids were dissolved in methanol (31). The solution was filtered, concentrated in vacuo and the resulting solid dried overnight in vacuo at 50° C. to give 287 g of material.

The majority of the material (285 g) was slurried overnight in acetone/water (4/1 by volume, 1.41), filtered, the solid was washed with acetone/water 4/1 (300 ml) and dried over 3 nights in vacuo at 50° C. to give 251 g of material.

The majority of the material was sieved through a 500 μM sieve to afford the title compound (242 g).
(ii) Form B Under nitrogen, to a stirred suspension of 4-amino-2-chloro-6,7-dimethoxy-5-(2-pyridyl)quinazoline (166 g, 0.53 mol) and N-(1,2,3,4-tetrahydro-5-isoquinolyl)-methanesulfonamide hydrochloride (152 g, 0.58 mol) in n-butanol (2.01) was added triethylamine (161 ml, 1.16 mol) and further n-butanol (1.31). The reaction was warmed to reflux and stirred at this temperature for 11 h. The reaction mixture was cooled to room temperature, concentrated in vacuo and the residue slurried in water (2.651) and sodium hydrogen carbonate (28.5 g) added. The resulting slurry was stirred overnight, filtered and the solid washed with water (500 ml). The resulting damp solid was added to methanol (4 1) and the resulting suspension concentrated in vacuo until a thick suspension was obtained. Further methanol (150 ml) was added, and resulting slurry filtered and washed with methanol (3×50 ml). The resulting solid was dried over 3 nights in vacuo at 41° C. The dried solid was then slurried overnight in acetone/water (¼ by volume, 1250 ml), filtered, the solid washed with acetone/water ¼ (3×50 ml) and dried over 2 nights in vacuo at 54° C. to afford the title compound (245 g).
(iii) Form C To a mixture of 4-amino-2-(5-methanesulfonamido-1,2,3,4-tetrahydro-2-isoquinolyl)-6,7-dimethoxy-5-(2-pyridyl) quinazoline (0.1 g of a batch of approximately 90% purity, a Form D/amorphous mixture, 1.7 mmol) and adipic acid (0.027 g, 1.8 mmol) was added acetone (1.25 ml) and the resulting suspension stirred at room temperature over 3 nights. The resulting suspension was filtered and dried overnight in vacuo at 48° C. to afford a quantity of the title compound.
(iv) Form E Under nitrogen, to a stirred suspension of 4-amino-2-chloro-6,7-dimethoxy-5-(2-pyridyl)quinazoline (105 g, 0.33 mol) in n-butanol (2.11) was added N-(1,2,3,4-tetrahydro-5-isoquinolyl)methanesulfonamide hydrochloride (152 g, 0.37 mol) and triethylamine (106 ml, 0.73 mol). The reaction was warmed to reflux and stirred at reflux for 6 h, cooled to room temperature and stirred overnight at room temperature. The mixture was then returned to reflux, stirred at reflux for 6 h and cooled to room temperature and stirred at room temperature overnight. The reaction mixture was then concentrated in vacuo and the residue slurried in water (1.681) and sodium hydrogen carbonate (17.9 g) added. The resulting slurry was stirred overnight, filtered, and the damp solid was added to acetonitrile (1.161). The resulting slurry was heated to reflux, then allowed to cool to room temperature and stirred at room temperature overnight. The resulting slurry was filtered and washed with acetonitrile (2×100 ml).

The damp solid was slurried in acetone/water (¼ by volume, 800 ml) overnight at room temperature, filtered, the solid washed with acetone/water ¼ (2×50 ml) and dried overnight in vacuo at 45° C. to give 158 g of material.

The majority of the material obtained from the above preparation (155 g) was combined with further portions of material (596 g) prepared in a similar manner and suspended in acetonitrile (5.281). The suspension was warmed to reflux, stirred at reflux for 90 min, cooled to room temperature and stirred at room temperature overnight. The solid was collected by filtration, washed with acetonitrile (100 ml) and dried overnight in vacuo at 50° C. to give the title compound (734 g).

Example 2

4-Amino-6,7-dimethoxy-2-(5-methanesulfonamido-1,2,3,4-tetrahydroisoquinol-2-yl)-5-(2-pyridyl)quinazoline mesylate (i) The salt formation process described below was used to process Form B free base to the methanesulfonate salt.

Under nitrogen, a suspension of Form B 4-amino-6,7-dimethoxy-2-(5-methanesulfonamido-1,2,3,4-tetrahydroisoquinol-2-yl)-5-(2-pyridyl)quinazoline (2.0 g) in butanone/water (10/1 by volume, 24 ml) was heated to reflux over 20 mins. Butanone/water 10/1 was added until a solution was achieved (an extra 3 ml was added, bringing the total solvent volume to 27 ml). The solution was left to cool to 50° C. and methanesulfonic acid (0.38 g, 4.0 mmol) was added dropwise over 30 seconds. The addition vessel was washed with butanone/water 10/1 (2×0.25 ml) and the washings were added to the reaction vessel. The resulting suspension was left to cool to room temperature and then stirred at this temperature for 2 h. The solid was collected by filtration, washed with acetone (2×2 ml), left to pull dry for 30 min and dried overnight in vacuo at 54° C. to afford the title compound (2.2 g) as a white solid.

$^1$H-NMR (300 MHz, DMSO) δ: 2.30 (3H, s), 2.99 (3H, s), 3.04 (2H, m), 3.44 (3H, s), 3.93 (2H, m), 4.01 (3H, s), 4.91 (2H, s), 7.15 (1H, d), 7.28 (2H, m), 7.44 (1H, s), 7.57 (2H, m), 8.02 (1H, m), 8.77 (1H, m), 9.19 (1H, s).

(ii) The following preparation was used to process Form E free base to the methanesulfonate salt.

A suspension of Form E 4-amino-6,7-dimethoxy-2-(5-methanesulfonamido-1,2,3,4-tetrahydro-2-isoquinolyl)-5-(2-pyridyl)quinazoline (1.0 g, 1.97 mmol) in acetone/water (12/7 by volume, 9.5 ml) was heated to reflux. Methanesulfonic acid (0.19 g, 1.99 mmol) was added in one portion. The addition vessel was washed with water (1 ml) and the resulting solution left to cool to room temperature overnight. The solid from the resulting suspension was collected by filtration and dried overnight in vacuo at 45° C. to afford the title compound (1.14 g) as a white solid.

Example 3

In vivo activity

The daily oral administration of 4-amino-6,7-dimethoxy-2-(5-methanesulfonamido-1,2,3,4-tetrahydroisoquinol-2-yl)-5-(2-pyridyl)quinazoline mesylate to male and female Sprague-Dawley rats at 30 mg/kg for 1 month induced changes linked to the pharmacological activity of the compound: however, there was no evidence of adverse effects.

What is claimed is:

1. 4-Amino-6,7-dimethoxy-2-(5-methanesulfonamido-1,2,3,4-tetrahydroisoquinol-2-yl)-5-(2-pyridyl)quinazoline mesylate of the formula

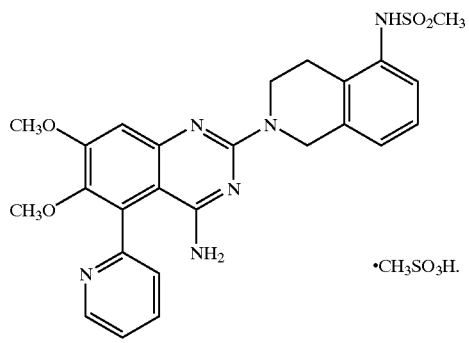

2. The 4-amino-6,7-dimethoxy-2-(5-methanesulfonamido-1,2,3,4-tetrahydroisoquinol-2-yl)-5-(2-pyridyl)quinazoline mesylate in accordance with claim 1, which exhibits an endothermic event at about 279° C. during differential scanning calorimetry or which exhibits a powder X-ray diffraction pattern obtained by irradiation with copper K-alpha$_1$ X-rays of wavelength 1.5406 Å, having the following main peaks:

| Angle 2-Theta ° | Intensity % |
|---|---|
| 7.392 | 22.9 |
| 14.733 | 22.6 |
| 14.813 | 40.1 |
| 17.694 | 31 |
| 18.964 | 40.5 |
| 19.297 | 57.9 |
| 20.265 | 51 |
| 21.414 | 40 |
| 22.136 | 24 |
| 22.934 | 32.8 |
| 23.842 | 49.4 |
| 24.795 | 100 |
| 27.012 | 30.3 |
| 28.673 | 22.3 |
| 29.305 | 24.6. |

3. 4-amino-6,7-dimethoxy-2-(5-methanesulfonamido-1,2,3,4-tetrahydroisoquinol-2-yl)-5-(2-pyridyl)quinazoline that contains more than 90% of a single crystalline free base polymorphic form, wherein the single polymorphic form exhibits an endothermic event at about 229° C. during differential scanning calorimetry, or a powder X-ray diffraction pattern obtained by irradiation with copper K-alpha$_1$ X-rays of wavelength 1.5406 Å, having the following main peaks:

| Angle 2-Theta° | Intensity % |
|---|---|
| 9.675 | 23.0 |
| 16.914 | 30.8 |
| 19.315 | 38.5 |
| 19.358 | 42.2 |
| 19.444 | 31.1 |
| 19.778 | 26.6 |
| 23.852 | 100.0 |
| 25.280 | 28.2 |
| 32.760 | 25.6. |

4. The crystalline free base polymorphic form of claim 3 wherein the crystalline free base polymorphic form contains more than 99% of the single polymorphic form.

5. A pharmaceutical formulation that comprises 4-amino-6,7-dimethoxy-2 (5-methanesulfonamido-1,2,3,4- tetrahydroisoquinol-2-yl)-5-(2-pyridyl) quinazoline mesylate of the formula

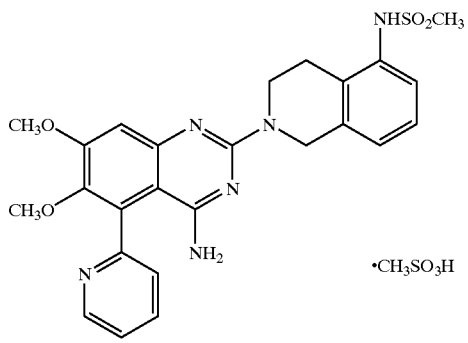

or 4-amino-6,7-dimethoxy-2-(5-methanesulfonamido-1,2,3,4-tetrahydroisoquinol-2-yl)-5-(2-pyridyl) quinazoline that contains more than 90% of a single crystalline free base polymorphic form, wherein the single polymorphic form exhibits an endothermic event at about 229° C. during differential scanning calorimetry or a powder X-ray diffraction pattern obtained by irradiation with copper K-alpha$_1$ X-rays of wavelength 1.5406 Å, having the following main peaks:

| Angle 2-Theta° | Intensity % |
|---|---|
| 9.675 | 23.0 |
| 16.914 | 30.8 |
| 19.315 | 38.5 |
| 19.358 | 42.2 |
| 19.444 | 31.1 |
| 19.778 | 26.6 |
| 23.852 | 100.0 |
| 25.280 | 28.2 |
| 32.760 | 25.6 | and a pharmaceutically acceptable carrier, vehicle or diluent.

6. A method of treating benign prostatic hyperplasia, the method comprising administering to a patient suffering therefrom a therapeutically effective amount of 4-amino-6,7-dimethoxy-2-(5-methanesulfonamido-1,2,3,4-tetrahydroisoquinol-2-yl)-5-(2-pyridyl)quinazoline mesylate of the formula

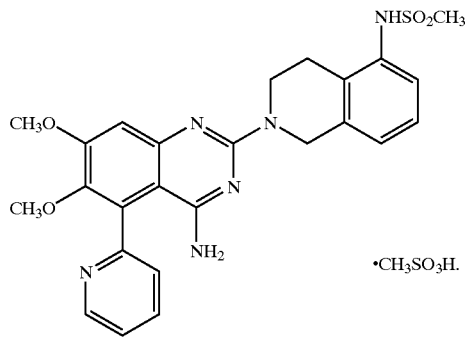

7. A method of treating benign prostatic hyperplasia, the method comprising administering to a patient suffering therefrom, a therapeutically effective amount of 4-amino-6,7-dimethoxy-2-(5-methanesulfonamido-1,2,3,4-tetrahydroisoquinol-2-yl)-5-(2-pyridyl)quinazoline that contains more than 90% of a single crystalline free base polymorphic form, wherein the single polymorphic form exhibits an endothermic event at about 229° C. during differential scanning calorimetry or a powder X-ray diffraction pattern obtained by irradiation with copper K-alpha$_1$ X-rays of wavelength 1.5406 Å, having the following main peaks:

| Angle 2-Theta° | Intensity % |
|---|---|
| 9.675 | 23.0 |
| 16.914 | 30.8 |
| 19.315 | 38.5 |
| 19.358 | 42.2 |
| 19.444 | 31.1 |
| 19.778 | 26.6 |
| 23.852 | 100.0 |
| 25.280 | 28.2 |
| 32.760 | 25.6. |

8. The method of claim 7 wherein the of 4-amino-6,7-dimethoxy-2-(5-methanesulfonamido-1,2,3,4-tetrahydroisoquinol-2-yl)-5-(2-pyridyl)quinazoline contains more than 99% of the single crystalline free base form.

* * * * *